(12) United States Patent
Palombi

(10) Patent No.: US 9,259,321 B2
(45) Date of Patent: Feb. 16, 2016

(54) FEMUR PROSTHETIC STEM WITH BACK GRASPING

(75) Inventor: Paolo Palombi, Rome (IT)

(73) Assignee: Paolo Palombi, Rome (IT)

( * ) Notice: Subject to any disclaimer, the term of this patent is extended or adjusted under 35 U.S.C. 154(b) by 0 days.

(21) Appl. No.: 13/635,107

(22) PCT Filed: Mar. 11, 2011

(86) PCT No.: PCT/IT2011/000069
§ 371 (c)(1),
(2), (4) Date: Dec. 27, 2012

(87) PCT Pub. No.: WO2011/114363
PCT Pub. Date: Sep. 22, 2011

(65) Prior Publication Data
US 2013/0138220 A1 May 30, 2013

(30) Foreign Application Priority Data

Mar. 15, 2010 (IT) .................... RM100036 U
Dec. 16, 2010 (IT) .................... RM10A0664

(51) Int. Cl.
*A61F 2/36* (2006.01)
*A61F 2/32* (2006.01)
*A61F 2/30* (2006.01)

(52) U.S. Cl.
CPC .............. *A61F 2/32* (2013.01); *A61F 2/3662* (2013.01); *A61F 2/3601* (2013.01); *A61F 2002/3082* (2013.01); *A61F 2002/30131* (2013.01);
(Continued)

(58) Field of Classification Search
CPC .............. A61F 2002/3645; A61F 2002/3631; A61F 2002/3668; A61F 2002/368; A61F 2002/3692; A61F 2002/3696; A61F 2002/3694; A61F 2002/3688; A61F 2002/3682; A61F 2/3662; A61F 2/3672; A61F 2002/30724; A61F 2002/30135; A61F 2002/30131; A61F 2002/30217; A61F 2002/3022; A61F 2002/30238; A61F 2002/30738; A61F 2002/30884; A61F 2002/30237; A61F 2002/30235; A61F 2002/30726
USPC .......... 623/23.15, 23.35, 20.36, 21.16, 22.11, 623/23.33, 23.26, 23.25, 23.18
See application file for complete search history.

(56) References Cited

U.S. PATENT DOCUMENTS 4,287,617 A * 9/1981 Tornier .................... 623/23.32
4,681,590 A * 7/1987 Tansey .................... 623/23.26
(Continued)

FOREIGN PATENT DOCUMENTS

DE 4421153 A1 * 12/1995
EP 0075378 A1 * 3/1983 ............... A61F 1/03
(Continued)

OTHER PUBLICATIONS

Kranz et al. referene, Production of hip joint endoprosthesis insertable in bone cavity of patients, Dec. 14, 1995, Patent Translate by EPO and Google, pp. 1-4.*
(Continued)

*Primary Examiner* — Thomas J Sweet
*Assistant Examiner* — Cheryl Miller
(74) *Attorney, Agent, or Firm* — Hickman Palermo Becker Bingham LLP

(57) ABSTRACT

The invention relates to a femur prosthetic stem (1) having a front portion and a back portion, said stem being characterized in that it has a back hollow portion (2).

10 Claims, 2 Drawing Sheets

(52) U.S. Cl.
CPC ............. *A61F2002/30136* (2013.01); *A61F 2002/30169* (2013.01); *A61F 2002/30884* (2013.01); *A61F 2002/368* (2013.01); *A61F 2002/3645* (2013.01); *A61F 2002/3668* (2013.01); *A61F 2002/3678* (2013.01); *A61F 2002/3686* (2013.01); *A61F 2002/3688* (2013.01); *A61F 2002/3692* (2013.01); *A61F 2230/0013* (2013.01); *A61F 2230/0047* (2013.01)

(56) References Cited

U.S. PATENT DOCUMENTS

| | | | | |
|---|---|---|---|---|
| 4,808,186 | A * | 2/1989 | Smith | 623/23.33 |
| 4,921,501 | A * | 5/1990 | Giacometti | 623/23.33 |
| 4,978,357 | A * | 12/1990 | Goymann et al. | 623/22.4 |
| 5,015,817 | A * | 5/1991 | Kranz | 219/121.14 |
| 5,156,628 | A * | 10/1992 | Kranz | 623/23.33 |
| 5,554,190 | A * | 9/1996 | Draenert | 128/898 |
| 5,571,203 | A * | 11/1996 | Masini | 623/22.46 |
| 5,658,352 | A * | 8/1997 | Draenert | 623/22.4 |
| 5,702,484 | A * | 12/1997 | Goymann et al. | 623/23.21 |
| 5,766,262 | A * | 6/1998 | Mikhail | 623/23.25 |
| 6,241,772 | B1 * | 6/2001 | Mackwood Ling et al. | 623/23.15 |
| 6,706,073 | B2 * | 3/2004 | Draenert et al. | 623/22.46 |
| 7,494,509 | B1 * | 2/2009 | Hershberger et al. | 623/23.35 |
| 2003/0120347 | A1 * | 6/2003 | Steinberg | 623/22.17 |
| 2005/0256585 | A1 * | 11/2005 | Park et al. | 623/23.14 |
| 2007/0250176 | A1 * | 10/2007 | Ragbir | 623/23.15 |
| 2008/0119942 | A1 * | 5/2008 | Mercuri et al. | 623/22.11 |
| 2008/0200990 | A1 * | 8/2008 | McTighe et al. | 623/22.42 |
| 2010/0069909 | A1 * | 3/2010 | Taylor | 606/82 |

FOREIGN PATENT DOCUMENTS

| | | | | |
|---|---|---|---|---|
| EP | 0257222 | A1 * | 3/1988 | A61F 2/30 |
| EP | 0354142 | A1 * | 2/1990 | A61F 2/36 |
| EP | 0617933 | A1 | 10/1994 | |
| EP | 1923021 | A2 | 5/2008 | |
| WO | 9321863 | A1 | 11/1993 | |
| WO | WO 9321863 | A1 | 11/1993 | |

OTHER PUBLICATIONS

PCT/IT2011/000069 International Search Report, Sep. 22, 2001, Paolo Palombi [IT].

* cited by examiner

FEMUR PROSTHETIC STEM WITH BACK GRASPING

The present invention relates to a femur prosthetic stem with back grasping.

More specifically, the present invention relates to a femur prosthetic stem for a total hip prosthesis with back grasping having a short stem, which allows to carry out conservative and minimally invasive interventions.

As is known, conventional prosthetic stems have been so far characterized by proximal metaphyseal grasping, by diaphyseal grasping or by total grasping. All the torques acting on the stem of the known solutions are absorbed by the thrust of the inner part of the prosthetic stem on the diaphyseal duct without any danger of tilting.

Recently, new stems have been produced which, with the aim of saving osseous capital involved in the implant, are built shorter (short stem) and fastened only to the metaphysis.

This type of stem although advantageous in solving some problems, having a reduced anchorage in the duct, may be subject to the forces generated by the torque created between the load on the femur head and the anatomical axis of the femoral metadiaphyses, creating a thrust of the back of the prosthesis to the proximal part of the cancellous metadiaphyseal that dominates it, with the result of a mobilization in the proximal direction of the back of the prosthesis which lever on the calcar region, risking that this thrust could turn into a shearing force.

In this context can be found the proposed solution according to the present invention, which allows to create a short femur prosthetic stem, having such a structure that facilitates a better meta-epiphyseal conservation and a greater secondary fixation.

Another purpose of the present invention is to create a femur prosthetic stem, having the back surface deeply modified, with the creation of a groove and two wings, which increase the bone-prosthesis contact surface, with a better osseointegration.

These and other results are obtained, according to the invention, using a femur prosthetic stem having a back hollow portion.

Therefore specific object of the present invention is a femur prosthetic stem having a front portion and a back portion, said stem being characterized in that it has a back hollow portion.

In particular, according to the invention, said prosthesis stem is made from a single block, preferably of titanium alloy.

Preferably, according to the invention, the back portion has two, divergent, side wings, defining a cavity between them.

In a particularly favorite solution of the present invention, the radius of curvature of the stem is constant, so that the surgeon can insert it in the femur bone with a constant curvature movement.

Additionally, according to the invention, said stem has a particularly longitudinal back profile compared to those currently in the market, creating an angle mainly perpendicular to the axis of the femur where it is inserted.

The invention will now be described by way of illustration but not limitation, with particular reference to the drawings of the attached figures, wherein.

Figure 1:
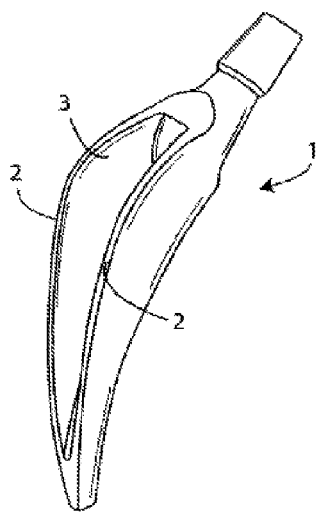
FIG. 1 shows a perspective view of the femur prosthetic stem with back grasping according to the invention.
Figure 2:
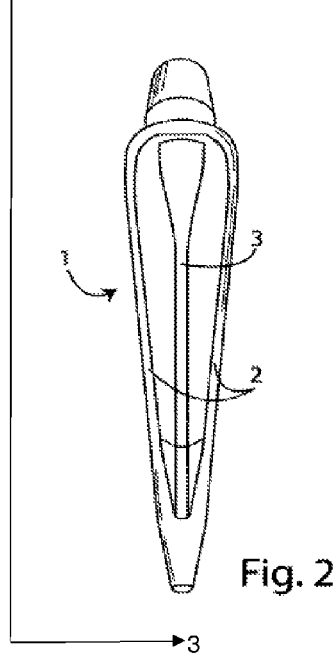
FIG. 2 shows a front view of the stem of FIG. 1.
Figure 3:
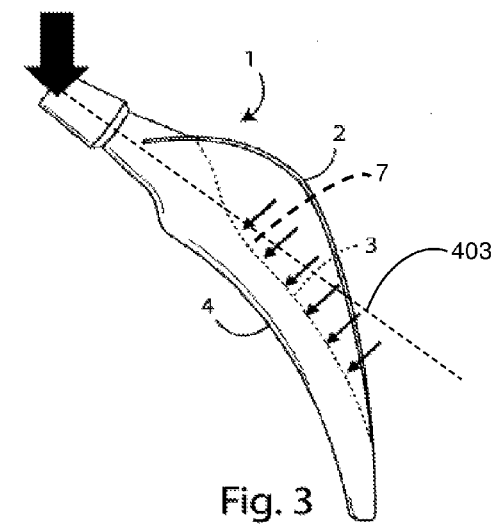
FIG. 3 shows a side view of the stem of FIG. 1.

Observing first the FIGS. 1, 2 and 3 of the attached drawings, it is shown a femur prosthetic stem 1 according to the invention, consisting of a single block, preferably in titanium alloy. Said stem 1 has on its back portion, two divergent side wings 2 that define a cavity 3.

Figure 4:
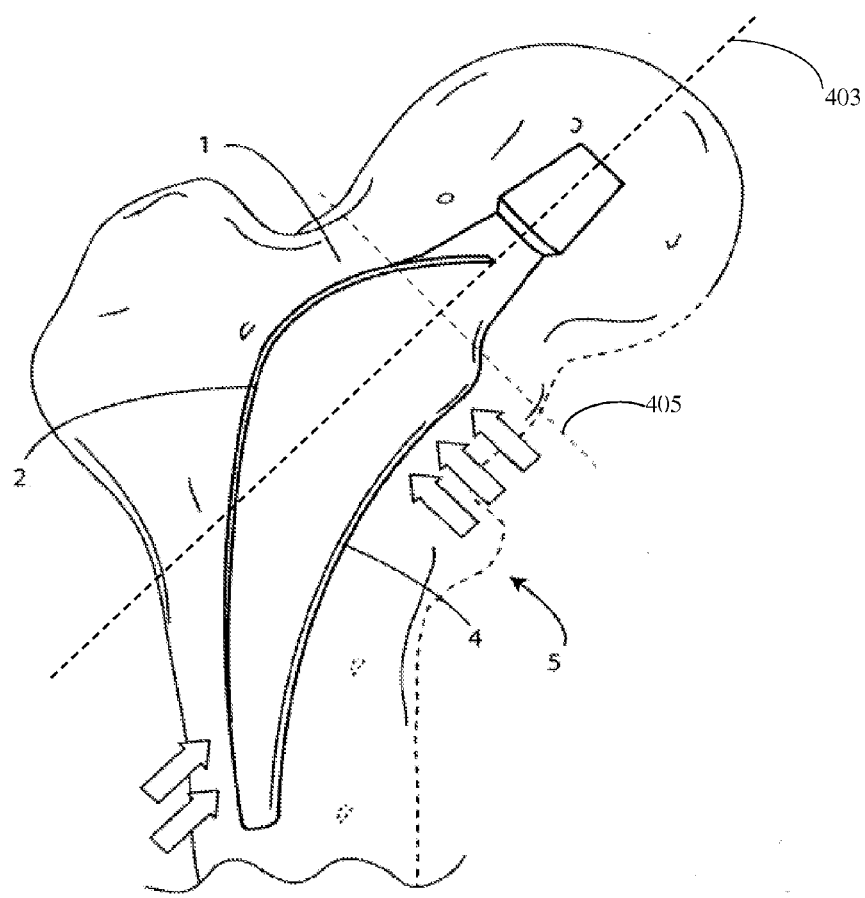
FIG. 4 shows a side view of the stem of FIG. 1 inserted into a femur.

As shown in FIG. 4, the radius of curvature 4 of the stem 1 has been designed to be always constant so that the surgeon can insert it in the femur bone 5 with a constant curvature movement, obtaining advantageously the integrity of the overlying metaphyseal bone.

Furthermore the stem 1 has a particularly longitudinal back profile compared to those currently in the market, creating an angle mainly perpendicular to the axis of the femur 5 where it is inserted. This makes it advantageously less movable under the stress of the torque. Moreover this allows to transform the vertical forces, resulting from the torque, into a more transversal thrust, addressing not only the problems of slipping, to which the stems on the market are subject, but also by redistributing the thrust along the back cavity 3 of the stem 1.

The stem 1 holds on the femur 5 both ventrally, as in the stems on the market, both dorsally where it is immersed in the cancellous bone of the femoral metaphysis, with a coupling reinforced by the two divergent side wings 2, which give resistance to the flexural stress and increase the contact/contrast surface bone-metal for an effective and rapid osseointegration; advantageously allowing to exert a torsional grip on the femur. In an embodiment, a back hollow portion of the stem is defined by two wings 2 and has a dorsal gutter portion 3. Each wing of the stem 1 has a convex profile along a length 403 of the stem 1. The dorsal gutter portion 3 has a portion 7 that is concave along the length 403 of the stem 1. Element 405 is a resection line along which a femur-head is cut and removed in order to insert the stem 1.

With the solution according to the present invention a series of important advantages are obtained. In particular, it is obtained a substantial saving of the bone affected by the intervention, an increase of the total area of bone contact, thanks to the two wings 2, a better integration (and thus a better fixation).

Furthermore a back grasping and a discharge of the stress are obtained thanks to the described configuration of the back of the stem.

Consequently, there is a saving of the bone in view of a possible revision of the prosthesis, a lower risk of "Aseptic loosening" of the stem, the possibility of achieving a less invasive intervention.

Moreover, the stem according to the invention allows to preserve the soft tissues, reducing hospitalization time and blood loss.

Therefore there is a reduction of the complications for the soft tissues, as it preserves the natural anatomy, and during the review phase for loss of bone matter.

Finally, the stem according to the invention is considerably lighter than the stems on the market, which consist of an entire block, thanks to the cavity along the back. The latter is of considerable advantage to the patient, because it improves the proprioception.

In the foregoing the preferred embodiments have been described and some variations of this invention have been suggested, but it should be understood that the skilled in the art may make modifications and changes without, however, leave the relative scope of protection, as defined by the attached claims.

The invention claimed is:

1. Femur prosthetic hollow stem having a length, the hollow stem comprising: a sidewall and a cavity; the sidewall having an interior surface defining the cavity and an opposing exterior surface; the sidewall comprising a base and two divergent wings, each wing having a free edge, wherein each free edge is convexly curved in a lengthwise direction along the length of the stem; wherein the two divergent wings converge at a distal end of the cavity; and wherein the interior surface of the base is concavely curved in a lengthwise direction along a portion of the length of the stem; wherein the hollow stem is characterized in that a radius of curvature of the stem is constant, so that a surgeon can insert the stem in a femur bone with a movement of constant curvature.

2. Stem according to claim 1, characterized in that the stem is made from a single block.

3. Stem according to claim 2, characterized in that the stem is made of titanium alloy.

4. Stem according to claim 1, characterized in that the two wings of a back portion define the cavity between the two wings.

5. Stem according to claim 1, characterized in that the stem has a particularly longitudinal back profile, creating an angle perpendicular to an axis of the femur when the stem is inserted.

6. Femur prosthetic hollow stem having a length, the hollow stem comprising: a sidewall and a cavity; the sidewall having an interior surface defining the cavity and an opposing exterior surface; the sidewall comprising a base and two wings, each wing having a free edge, wherein each free edge is convexly curved in a lengthwise direction along the length of the stem; wherein the interior surface of the base has a profile extending in a lengthwise direction along the length of the stem from a proximal end of the cavity to a distal end of the cavity, the profile comprising a first convex curve segment adjacent to the proximal end, a second convex curve segment adjacent to the distal end, and a concave curve segment in-between the first convex curve segment and the second convex curve segment wherein the hollow stem is characterized in that a radius of curvature of the stem is constant, so that a surgeon can insert the stem in a femur bone with a movement of constant curvature.

7. Stem according to claim 6, characterized in that the stem is made from a single block.

8. Stem according to claim 7, characterized in that the stem is made of titanium alloy.

9. Stem according to claim 6, characterized in that the two wings of a back portion define the cavity between the two wings.

10. Stem according to claim 6, characterized in that the stem has a particularly longitudinal back profile, creating an angle perpendicular to an axis of the femur where when the stem is inserted.

* * * * *